United States Patent [19]

McGovern et al.

[11] Patent Number: 4,761,280

[45] Date of Patent: Aug. 2, 1988

[54] ADDITIVES USEFUL AS CRYSTALLIZATION INHIBITORS AND ACTIVITY EXTENDERS FOR TRIMEDLURE, THE MEDITERRANEAN FRUIT FLY ATTRACTANT

[75] Inventors: Terrence P. McGovern, Bowie; Barbara A. Leonhardt, Potomac, both of Md.; Roy T. Cunningham, Hilo, Hi.

[73] Assignee: The United States of America as represented by the Secretary of Agriculture, Washington, D.C.

[21] Appl. No.: 904,533

[22] Filed: Sep. 8, 1986

[51] Int. Cl.[4] ............................................. A01N 25/00
[52] U.S. Cl. ....................................................... 424/84
[58] Field of Search .......................................... 424/84

[56] References Cited

U.S. PATENT DOCUMENTS 3,016,329  1/1962  Beroza et al. ........................ 424/84

OTHER PUBLICATIONS

T. P. McGovern, M. Beroza, K. Ohinata, D. Miyashita, and L. F. Steiner, "Volatility and Attractiveness to the Mediterranean Fruit Fly of Trimedlure and Its Isomers, and a Comparison of Its Volatility with that of Seven Other Insect Attractants," *Journal of Economic Entomology*, 59(6): 1450–1455, (1966).

T. P. McGovern and M. Beroza, "Effect of Fixatives and Other Chemicals in Extending the Activity of the Insect Attractant Trimedlure," *Journal of Economic Entomology*, 60(2): 379–383, (1967).

S. Nakagawa, E. J. Harris, and I. Keiser, "Performance of Capilure in Capturing Mediterranean Fruit Flies in Steiner Plastic or Cardboard Sticky Traps," *Journal of Economic Entomology*, 74: 244–245, (1981).

M. Beroza, N. Green, and S. I. Gertler, "New Attractants for the Mediterranean Fruit Fly," *Agricultural and Food Chemistry*, 9(5): 361–365, (1961).

T. P. McGovern and M. Beroza, "Structure of the Four Isomers of the Insect Attractant Trimedlure," *Journal of Organic Chemistry*, 31: 1472–1477, (1966).

B. A. Leonhardt, T. P. McGovern, and J. R. Plimmer, "Capillary GC Analysis of Trimedlure, the Attractant for the Medfly," *Journal of High Resolution Chromatography and Chromatographic Communications*, 5: 430–431, (1982).

T. P. McGovern, R. T. Cunningham, and B. A. Leonardt, "Attractiveness of Trans–Trimedlure and Its Four Isomers in Field Tests with the Mediterranean Fruit Fly (Diptera: Tephritidae)," *Journal of Economic Entomology*, (in Press).

S. Nakagawa, R. T. Cunningham, and T. Urago, "The Repellent Effect of High Trimedlure Concentrations in Plastic Traps to Mediterranean Fruit Fly in Hawaii," *Journal of Economic Entomology*, 64: 762–763, (1971).

N. Green and M. Beroza, "Cis–Trans Isomers of 6-Methyl-3-Cyclohexene-1-Carboxylic Acid and Their Sec-Butyl Esters," *Journal of Organic Chemistry*, 24: 761–764, (1959).

T. P. McGovern, R. T. Cunningham, and B. A. Leonhardt, "Cis-Trimedlure: Attraction for the Mediterranean Fruit Fly (Diptera: Tephritidae) and Isomeric Structural Assignments," *Journal of Economic Entomology*, 79: 98–102, (1986).

E. J. Harris, S. Nakagawa, and T. Urago, "Sticky Traps for Detection and Survey of Three Tephritids," *Journal of Economic Entomology*, 64(1): 62–65, (1971).

B. A. Leonhardt, R. E. Rice, E. M. Harte, and R. T. Cunningham, "Evaluation of Dispensers Containing Trimedlure, the Attractant for the Mediterranean Fruit Fly (Diptera: Tephritidae)," *Journal of Economic Entomology*, 77: 744–749, (1984).

*Primary Examiner*—Albert T. Meyers
*Assistant Examiner*—John M. Kilcoyne
*Attorney, Agent, or Firm*—M. Howard Silverstein; John Fado; Margaret A. Connor

[57] ABSTRACT

Certain esters of 4(and 5)-chloro-trans-2-methylcyclohexanecarboxylic acid act in a dual and advantageous capacity when added to the Mediterranean fruit fly attractant, trimedlure. They greatly reduce or eliminate crystallization of the solid trimedlure isomers that occurs on storage or use during cool weather and they significantly extend the attractive activity of trimedlure.

17 Claims, No Drawings

ADDITIVES USEFUL AS CRYSTALLIZATION INHIBITORS AND ACTIVITY EXTENDERS FOR TRIMEDLURE, THE MEDITERRANEAN FRUIT FLY ATTRACTANT

BACKGROUND OF THE INVENTION

1. Field of the Invention

This invention relates to additives for use with the Mediterranean fruit fly attractant, trimedlure, 1,1-dimethylethyl 4(and 5)-chlorotrans-2-methylcyclohexanecarboxylate. In particular, it relates to certain esters of 4(and 5)-chloro-trans-2-methylcyclohexanecarboxylic acid and their ability to act as inhibitors to the formation of crystalline masses in trimedlure as well as their ability to extend the attractive duration of trimedlure when mixed with the attractant.

2. Description of the Art

The Mediterranean fruit fly [*Ceratitus capitata* (Wiedemann)] commonly known as the medfly, is one of the worst pests of stonefruit and citrus fruits and vegetables, and presents a major threat to fruit and vegetable production in areas with mild winters. Although infestations of the medfly are primarily in Hawaii and subtropical regions of the continent, periodic invasions onto the mainland United States have resulted in great economic losses.

Insect attractants have proved to be invaluable tools for the control of insect species. Beroza et al. (*Agricultural and Food Chemistry* 9(5): 361–365 (1961)) reported that certain esters prepared from a mixture of the isomeric acids 4(and 5)-chloro-trans-2-methylcyclohexanecarboxylic acid were superior attractants for the medfly. First medlure, 1-methylpropyl 4(and 5)-chloro-trans-2-methylcyclohexanecarboxylate, then trimedlure, 1,1-dimethylethyl 4(and 5)-chlorotrans-2-methylcyclohexanecarboxylate, were utilized by Federal and state agencies as the standard survey and detection lure for the medfly in replacement of siglure, 1-methylpropyl trans-6-methyl-3-cyclohexenecarboxylate. Trimedlure has also been used for many years as the standard medfly attractant wherever the fly is or threatens to become established worldwide.

Commercial trimedlure consists mainly (90–95%) of the four isomers that have the methyl and ester substituents on the ring in the trans position, denoted as A, $B_1$, $B_2$, and C and ca. 5–10% of the four cis-isomers. The approximate analysis of these four trans-isomers in a typical trimedlure mixture was reported to be about 35% A, 15% $B_1$ and $B_2$, and 50% C. At room temperature A and $B_1$ are liquids., $B_2$ and C solids. (McGovern et al., *Journal of Organic Chemistry* 31: 1472–1477 (1966a); Leonhardt et al., *Journal of High Resolution Chromatography and Chromotography Communications* 5: 430–431 (1982).

Two serious problems exist that prevent the most economic and efficient use of trimedlure and both are seasonally related. The first problem is that trimedlure readily forms crystals, both in storage drums and in the dental wick dispensers, during cool weather. Occasionally, crystal formation even occurs in warm weather. Agencies responsible for detecting entry into the United States of agricultural pests such as the medfly must stockpile and store trimedlure for extended periods. It must be readily available for normal survey and detection purposes as well as for the intensified trapping that is required after eradication efforts have been carried out as was recently experienced in California and Florida. When crystals form in storage containers they remain as a solid mass at the bottom of the container. The crystalline cake will not dissolve, even at summer temperatures, without a considerable amount of external heating and agitation. Crystal formation on the wick dispensers seriously interferes with rebaiting procedures. The encrusted wick cannot smoothly and rapidly absorb the applied retreatment dosage resulting in lost time and frequently in trap contamination, thereby reducing the efficiency of the trap.

The method presently used to minimize crystallization problems is costly and counterproductive. Two grades of trimedlure are currently used for survey and detection purposes, a summer and a winter grade. Summer grade is the normal isomer blend as derived from the synthesis and is prone to crystal formation. Winter grade has crystals removed prior to use and is prepared by cooling summer grade trimedlure to $-5°$ C., seeding, and then filtering off all crystals that have formed after 24 hours. This procedure results in a considerable loss of material (ca. 30–40%) and in increased costs as well as loss of the isomer most attractive to the medfly. The crystalline "sludge" that is removed to prepare winter grade trimedlure is composed mainly of the C isomer, a solid when in pure form. Field tests and olfactometer tests have shown that isomer C is the most attractive and persistent isomer (McGovern et al., *Journal of Economic Entomology* 59: 1450–1455 (1966b); McGovern et al., *Journal of Economic Entomology*, 80: 617–620 (1987), thus its artificial removal greatly reduces the efficiency of the lure. A second problem is that during the hot weather season the persistence of trimedlure is short, thus requiring frequent trap rebaitings. Because of the size of the most efficient medfly trap, the excessive volatility of trimedlure, and the maximum allowable size of the dental wick dispensers, the standard trapping procedure is to rebait a trap every two weeks during the hot season by applying a 2 ml dose of trimedlure to saturate the dispenser. Crystallization on the wick interferes with rebaiting.

McGovern et al., 1966b, supra, first proposed the use of inert (nonattractive), volatile additives which would depress the formation of the solid form of trimedlure, i.e., inhibitors of crystallization. Desirable criteria stated for an inert, volatile material are that it does not interfere with the potency of the lure and that it evaporates at about the same rate as the lure. The best of the materials tested, diethyl butylmalonate, depressed crystal formation to some extent but also reduced the attractiveness of the lure.

The authors also reported the use of pentadecanolide, a perfume fixative, as an additive that depressed the volatility of trimedlure and thereby extended the duration of effectiveness of trimedlure, i.e., an activity extender. This material was not effective in extending the activity of siglure or cue-lure [4-(p-hydroxyphenyl)-2-butanone, acetate, the attractant for the melon fly, *Dacus cucurbitae* Coquillett]. Because pentadecanolide is too costly for practical use, other inert, non-volatile materials were tested as activity extenders (McGovern et al., *Journal of Economic Entomology* 60(2): 379–383 (1967)). While several materials were found to be effective, no specific structure was found preferable for depressing the volatility of trimedlure.

Since then, a commercial product called Capilure that contains a mixture of trimedlure and extenders, has been tested and marketed. While this material extended the effectiveness of trimedlure alone, a serious deficiency of this type of system, which employs a 25% or greater quantity of a non-volatile, nonattractive ingredient, is the accumulation of this material in a dispenser of limited capacity as rebaiting occurs. An alternate choice of dispenser replacement at each treatment adds to the cost.

SUMMARY OF THE INVENTION

We have found that certain esters of 4(and 5)-chloro-trans-2-methylcyclohexanecarboxylic acid act in a dual and advantageous capacity when added to trimedlure: (1) they inhibit, that is, greatly reduce or eliminate, crystallization of the solid trimedlure isomers that occurs on storage or use in cool weather, and (2) they significantly extend the attractive activity of trimedlure.

In the method of the invention, esters having 11 to 16 carbon atoms and containing a 4(and 5)-chloro-trans-2-methylcyclohexanecarboxclic acid moiety, are added to trimedlure. Surprisingly, these compounds not only inhibit the irreversible precipitation of the crystalline trimedlure isomers, they significantly extend the attractive duration of trimedlure.

Certain of the novel additives prevent crystal formation at moderately cool temperatures. At cold temperatures, crystals form but rapidly redissolve when allowed to come to room temperature without agitation. The additives when mixed with trimedlure provide an attractant composition that persists with high levels of activity up to two times that of standard trimedlure without adversely affecting the efficacy of the lure.

Because use of the invention results in elimination of the crystallization problem and the significant reduction in the labor intensive requirement for trap rebaiting services, these factors along with reduced use of attractant results in a substantial cost reduction for the program.

Additionally, because use of the additive of the invention lowers the rate of evaporation of trimedlure, higher doses can be used without inducing a repellent effect.

In accordance with this discovery, it is an object of the invention to provide additives which both inhibit crystallization and extend the activity of the medfly attractant, trimedlure.

Another object of this invention is to provide a medfly attractant composition that is longer lasting than standard trimedlure alone.

It is a further object to provide an additive for use with trimedlure which lowers the evaporation rate of trimedlure in the trimedlure plus additive mixture and thereby allows usage of high doses of trimedlure without causing a repellent effect.

Other objects and advantages of the invention will become readily apparent from the ensuing description.

DETAILED DESCRIPTION OF THE INVENTION

The compounds useful for inhibiting crystallization and extending the attractive duration of trimedlure are esters of 4(and 5)-chlorotrans-2-methylcyclohexanecarboxylic acid. The compounds of the invention are represented by the general formula (I)

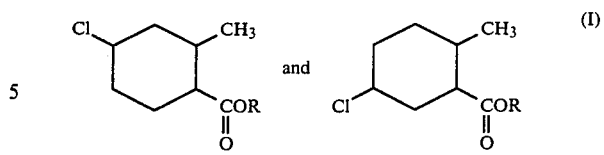

wherein —$CH_3$ and —COOR are in the trans-configuration and the Cl is in both an equatorial and axial conformation, thus providing four isomers, and R is a $C_4$ to $C_6$ straight- or branched-chain alkyl but not 1,1-dimethylethyl, $C_4$ to $C_6$ straight- or branched-chain alkenyl, $C_1$ or $C_2$ straight-chain alkyl which is substituted with a $C_3$ to $C_5$ alicyclic ring moiety which in turn is optionally substituted with lower alkyl, or a $C_3$ to $C_6$ alicyclic ring structure which is optionally substituted with lower alkyl.

According to the present invention, the expression lower alkyl means a group containing 1 to 3 carbon atoms, either straight- or branched-chain, but preferably 1 carbon atom.

It is within the compass of the invention to use a single isomeric mixture, i.e., where R represents a single moiety, as described above by the general formula (I) or to use combinations of two or more of these isomeric mixtures, i.e., where R represents two or more different moieties.

Typical examples of compounds useful in the method of the invention are the following:

A. Alkyl 4(and 5)-chloro-trans-2-methylcyclohexanecarboxylates wherein the $C_4$ to $C_6$ straight- or branched-chain alkyl group is 1-methylpropyl, 2-methylpropyl, 1,1-dimethylpropyl, 1-ethylpropyl, butyl, 1-methylbutyl, 2-methylbutyl, 3-methylbutyl, 1-ethylbutyl, 2-ethylbutyl, 1,3-dimethylbutyl, pentyl, 1-methylpentyl, 2-methylpentyl, or hexyl.

B. Alkenyl 4(and 5)-chloro-trans-2-methylcyclohexanecarboxylates wherein the $C_4$ to $C_6$ straight- or branched-chain alkenyl group is 2-butenyl, 2-pentenyl, 1-methyl-2-propenyl, 1-ethyl-2-propenyl, 1-methyl-3-butenyl, 1-methyl-2-butenyl, 1,1-dimethyl-2-propenyl, 3-butenyl, 3-pentenyl, 4-pentenyl, or 2-hexenyl.

C. Alicyclic alkyl 4(and 5)-chloro-trans-2-methylcyclohexanecarboxylates wherein R is 1-cyclopropylethyl.

D. Alicyclic 4(and 5)-chloro-trans-2-methylcyclohexanecarboxylates wherein the $C_3$ to $C_6$ alicyclic ring is cyclopropyl, cyclopentyl or cyclohexyl.

The compounds of the invention may be prepared according to known procedures outlined by Beroza et al., supra, and Green et al. (*Journal of Organic Chemistry* 24: 761–764 (1959)). The general reaction scheme may be outlined as follows: the 4(and 5)-chloro-trans-2-methylcyclohexanecarboxylic acid is converted to the acid chloride by reacting it with thionyl chloride under mild conditions, i.e., the reaction product is stripped of its solvent in vacuo on a warm water bath and the acid chloride is not distilled. The esters are prepared by reacting the acid chloride with the appropriate alcohol in the presence of pyridine in a suitable solvent such as benzene or anhydrous ethyl ether and working up by sequential extraction using dilute (5%–10%) aqueous hydrochloric acid and sodium hydroxide and then washing with saturated salt solution until neutral to litmus proper. The crude product is dried over anhydrous magnesium sulfate, filtered, and the solvent removed. Final purification is accomplished by fractional distillation under high vacuum.

As stated above, the compounds of the invention are useful, when mixed with trimedlure, to inhibit the irreversible precipitation of the crystalline trimedlure isomers and to significantly extend the attractive duration of trimedlure. The mixture of the additives and trimedlure is also attractive to the medfly and longer lasting than the standard trimedlure. Because the additives of the invention are of lower volatility than trimedlure, they have the capacity to retard the evaporation rate of trimedlure.

In order to achieve inhibition of crystal formation and extension of the attractive duration of trimedlure, the compounds of the invention are added to trimedlure in an effective amount. In the case of inhibition of crystal formation, a crystallization inhibiting amount is defined as that quantity of compound which when added to trimedlure greatly reduces or eliminates the irreversible precipitation of the crystalline trimedlure isomers. The term irreversible, for purposes of the invention, means that, once formed, crystals do not completely redissolve unless external heating above ambient room temperature and agitation are applied. In the case of extension of the attractive duration of trimedlure, an attraction extending amount is defined as that quantity of additive which when added to trimedlure attracts male medflies to the mixture of additive plus trimedlure for a duration of at least 20% greater than for trimedlure alone, and during the period attraction is extended, the mixture attracts male medflies at a rate significantly higher than males are attracted to trimedlure alone.

Under typical conditions, amounts of at least about 12.5% additive on a volume/volume basis of additive/trimedlure are effective to both inhibit crystal formation and extend the activity of trimedlure. When used according to the invention, the compounds must be in a pure or substantially pure form, that is, the compounds must be substantially free of undesirable masking or inhibitory effects with regard to crystallization inhibiting and attraction extending activities. The compounds may be applied undiluted or in solution with a suitable carrier such as an organic solvent.

Similar to other insect attractants, the mixture of additives of the invention plus trimedlure can be used as a trap bait or otherwise applied to a locus in an amount effective for attracting, monitoring, or detecting medflies. It is within the compass of the invention to use the additive plus trimedlure composition in combination with control agents for the medfly, such as insecticides, chemosterilants, and the like.

The crystal inhibiting properties and the biological activity of the additives were demonstrated by practical laboratory and field tests. The crystal inhibiting properties were demonstrated in laboratory tests in which the additive plus trimedlure mixture and standard trimedlure were cooled to various temperatures for designated time periods as described in Example 1 below. The amount of crystal formation was noted and the samples were allowed to warm to ambient room temperature. The crystal content of each sample was again recorded. The observations are listed in Table 1. Although trimedlure contains ca. 55–70% of the solid isomers $B_2$ and C, the entire sample of standard trimedlure solidifies at cool temperatures (ca. 3° C. and below). At the moderate temperatures of 16° to 6° C. trimedlure has almost completely solidified and only redissolved slightly when returned to room temperature. At the cold and very cold temperatures of $-10°$ C. and $-23°$ C. both trimedlure and trimedlure plus additive appear completely solid. However, while trimedlure remained mostly solid after returning to room temperature, the sample with additive had only a trace of crystals remaining, even with no agitation. The lower temperatures are extremes and are unrealistic as either testing or storage temperatures. They do however serve to illustrate the effectiveness of the compounds to inhibit the irreversible crystallization of trimedlure. At the more realistic temperature of 10° C., the additive prevents the formation of crystals.

The ability of the additives to extend the attractiveness of trimedlure without adversely affecting its level of activity has been demonstrated by practical field tests. Attractiveness data for the mixtures, the pure additives, and a standard trimedlure are presented in Table 2. The additives tested include the following esters of 4(and 5)-chloro-trans-2-methylcyclohexane-1-carboxylic acid: 1,1-dimethylpropyl ester (A-1); 1-methylbutyl ester (A-2); 1-methylpropyl ester (A-3); and 1,1-dimethyl-2-propenyl ester (A-4). The data on Table 2 begins after each lure was aged 11 days. There were five examinations of the trap catches of each lure prior to day 11. The catches of all of the mixtures at all of the examinations, with the exception of the 50% A-4 mixture on two occasions, were not statistically different ($P=0.05$) from that of the standard trimedlure. This shows that the additives do not adversely affect the attractiveness of trimedlure.

The standard trimedlure treatment starts with a larger dosage of trimedlure than do the mixtures but between days 4 to 8 most of the mixtures had about the same or larger quantity of trimedlure than did the standard. The relative levels of trimedlure in each lure then remained about the same through day 11. This shows the volatility depressant qualities of the additives. The activity extending qualities of the additives are shown by the data obtained after day 11 when the attractiveness of the standard trimedlure began to fail. On day 14 all of the catches of the mixtures were statistically superior to that of the standard trimedlure. This was also true of day 18 with the exception of the 12.5% mixtures using A-1, A-3, and A-4. Several of the mixtures still provided high medfly catches after 23 days of aging. In summary, the data in Table 2 clearly demonstrate that the additives of the invention significantly extend the attractive duration of trimedlure without adversely affecting its level of activity.

The relative attraction of trimedlure and trimedlure plus 25% A-2, and the variation in lure content of their wick dispensers over time was tested in the field. The data are presented in Table 3. The first section of the table gives the medfly catch data for trimedlure and trimedlure plus additive. Through two weeks both lures are statistically equivalent, however, at weeks 4 and 5 the trimedlure plus additive is statistically superior to trimedlure alone. The second section of Table 3 discloses even more clearly the activity extending properties of the additive. In the first instance the trimedlure wicks contained an average of 627 mg more trimedlure initially than did the wicks containing trimedlure plus additives. After two weeks, the trimedlure plus additive lure contained more trimedlure than the trimedlure "only" wick. Through weeks 1 and 2 the trimedlure wick released 794 and 729 mg of trimedlure/wick, respectively (1523 mg total), while the lure with additive released 441 and 322 mg of trimedlure/wick, respectively (763 mg total). This represents about a 50% reduction in the amount of trimedlure evaporated with no loss of efficiency. Inasmuch as the two lures are equally effective through two weeks, the 627 mg of excess trimedlure initially contained in the trimedlure only wick can be looked on as wasted lure. This amounts to about one third of the initial dose which translates to a significant cost factor. The trimedlure plus additive wicks lost a total of 871 mg of combined lure. Thus, it can be seen that incorporating an additive of the invention into a trimedlure formulation decreases the overall evaporation rate of the lure relative to trimedlure alone and, as trimedlure becomes depleted, the rate of evaporation of the mixture approaches that of the additive. Because some of the novel additives are attractive to the medfly itself, high levels of attraction can continue until the additive is completely depleted.

In the preferred embodiment of the invention the additives, themselves, are attractants for the medfly. This has the advantages that the entire mixture is attractive to the medfly, and the wick does not accumulate inactive materials. The level of attraction that is possessed by seven of the compounds themselves is illustrated by the data in Table 4. Although five of the compounds are significantly less attractive than trimedlure at the beginning of the test (day 1), by day 8 all have become significantly more attractive than trimedlure.

It has been shown that high concentrations of trimedlure are repellent to the medfly (Nakagawa et al., Journal of Economic Entomology 64: 762–763 (1971)). Use of the additives of the invention are also beneficial in a situation where high dosages of trimedlure are considered for long term use. The lower rate of trimedlure evaporation achieved with the additive allows higher dosages to be used without inducing a repellent effect. For example, referring to Table 3, it is shown that, from week 1 to 2, trimedlure lost 729 mg of lure while trimedlure plus additive at week 0 to 1 (the time when both lures had about the same amount of trimedlure) lost 441 mgms of trimedlure. This amounts to approximately a 40% reduction in the volatilization of trimedlure.

As shown above, a number of significant advantages are gained by using a mixture of trimedlure plus an additive of the invention when compared with the use of trimedlure alone. These are:

A. Crystal formation problems associated with trimedlure storage are eliminated.

B. Crystal formation in and on the surface of wicks used in field traps either during cool weather or as evaporation proceeds with the loss of more volatile, liquid isomers is eliminated.

C. The life of the lure is extended at a significantly higher level of attraction at least 20% longer than trimedlure alone resulting in the potential for less trap servicing requirements.

D. Improved economies in the use of trimedlure and in the synthesis of trimedlure plus additive are achieved:

(1) The rate of loss of trimedlure from a dispenser is greatly reduced.

(2) The need for a special and more expensive winter grade trimedlure is eliminated. This not only reduces cost but results in an isomer blend that is richer in the most attractive isomer.

(3) Since the additive is an ester analog of trimedlure it can be synthesized in the same reaction vessel as trimedlure by using the proper binary alcohol mixture. An alternate approach is to carry out the standard synthesis until the esterification step as is usually done for trimedlure, then trimedlure and the additive ester can be prepared separately (using the same acid chloride) and formulated later. These economies that can be achieved in the synthesis of the trimedlure plus additive mixture (single use of equipment, reduced time for manufacture, use of a common intermediate) cannot be duplicated with a structurally dissimilar additive.

(4) The significantly lower evaporation rate of trimedlure in the trimedlure plus additive mixture will reduce the potential for repellency that is observed at high dosages. Thus the scope for the use of trimedlure is broadened.

E. Where the additive, itself, is attractive, the entire mixture is attractive to medflies, and the wick does not accumulate inactive, non-volatile materials.

EXAMPLES

The following examples are intended only to further illustrate the invention and are not intended to limit the scope of the invention which is defined by the claims.

EXAMPLE 1

Additives. The following esters of 4(and 5)-chloro-trans-2-methylcyclohexane-1-carboxylic acid: 1,1-dimethylpropyl ester (A-1); 1-methylbutyl ester (A-2); 1-methylpropyl ester (A-3); and 1,1-dimethyl-2-propenyl ester (A-4), were synthesized according to the nonepimerizing method of Beroza et al. as described above and purified by distillation under high vacuum (A-1, b.p. 80° C./0.35 mm Hg, $n_D^{25}$ 1.4600; A-2, b.p. 73°–74° C./0.075 mm Hg, $n_D^{25}$ 1.4582; A-3, b.p. 62°–63° C./0.05 mm Hg, $n_D^{25}$ 1.4573; A-4, b.p. 63° C./0.075 mm, $n_D^{25}$ 1.4685). Their purity was determined to be 98+% by gas chromatography.

The general synthesis of the additives is illustrated by the preparation of A-2:

48.5 g of 4(and 5)-chloro-trans-2-methylcyclohexane-1-carbonyl chloride (0.25 mole) in 50 ml benzene was added dropwise with stirring to a cold solution (ice-bath) of 24.2 g of 2-pentanol (0.275 mole) and 19.8 g of pyridine in 100 ml of benzene. After the addition was complete the reaction mixture was allowed to come to room temperature and then heated under reflux for two hours. The cooled reaction mixture was poured into water to remove the by-product pyridinium hydrochloride and then was extracted with 5% hydrochloric acid and 5% sodium hydroxide aqueous solutions and finally was washed with a saturated salt solution. The benzene solution was dried over anhydrous magnesium sulfate, filtered, and the solvent was removed under reduced pressure on a Rota-vac. Final purification was accomplished by fractional distillation under high vacuum, b.p. 73°–74° C./0.075 mm Hg, $n_D^{25}$ 1.4582, recovered yield 45.7 g.

Trimedlure. The trimedlure used in the tests was a summer grade preparation that was obtained commercially (UOP, East Rutherford, NJ). It has been used for several years as a "standard" attractant in continuing attractancy tests conducted in Hawaii by USDA scientists.

Analysis: Capillary and packed column gas chromatography analyses of trimedlure and the additives were conducted as described by Leonhardt et al., 1982, supra.

Test for inhibition of crystal formation. The additives were mixed in concentrations of 12.5, 25.0 and 50.0% with the standard trimedlure (v/v, additive/trimedlure). A 4.0 ml sample (height of liquid 33 mm) of each mixture and the standard trimedlure were placed in a clear vial (4.4 cm high×1.2 cm ID) which was then capped and placed in a freezer. After cooling 1 hour each sample was seeded with a few minute crystals of trimedlure-isomer C to induce crystal formation and then returned to the freezer without mixing. The samples were held overnight at a prescribed temperature. Eight different temperatures were used: +24°, +16°, +6°, +3°, −10°, −13°, −19°, and −23° C. The next day the samples were removed from the freezer and the height of the crystalline mass was measured after 0, 1, 2, 3, and 4 hours standing at room temperature with no mixing. Samples that had crystals remaining after 4 hours were warmed to redissolve the crystals. The sequency was repeated at each of the eight test temperatures using the same samples.

The results of the effect of the additives on crystal formation of trimedlure are given in Table 1. The height of the crystalline masses through four hours postcooling are listed for four temperatures which are representative of the eight temperatures used. As discussed in detail above, the data demonstrate that the compounds are effective in inhibiting the irreversible crystallization of trimedlure.

method described in McGovern et al. (*Journal of Economic Entomology* 79: 98–102 (1986)). A dosage of 200 μl of the standard trimedlure and each mixture were applied undiluted to cotton wicks (9.5 mm diam.×12.7 mm length; Johnson and Johnson No. 2) in standard Jackson traps (Harris et al., *Journal of Economic Entomology* 64: 62–65 (1971)). Traps were hung on the trees in a randomized complete block design. Ten replicates were used in the attractancy tests; additional wicks were aged at the same location and were used for determination by gas chromatography of the representative lure content at prescribed time periods throughout the test. Sterile laboratory-reared medflies were released throughout the test plot in a uniform manner at 0, 2, 4, 8, 9, 11, 14, 16, 18, 21, and 23 days posttreatment. Fresh sticky inserts were placed in the traps prior to each release and remained in the trap throughout the test interval. At days 21 and 23 posttreatment, a wick freshly treated with trimedlure was introduced into the test. Data were analyzed by analyses of variance, and means were separated by Duncan's multiple range test at the P=0.05 level (Duncan, *Virginia Journal of Science* 12: 171–189 (1951)).

Analysis: Isolation and analysis of the residual lure content in the aged wicks are performed as described in

TABLE 1

| % A | Hr Post Cooling | Height (mm) of crystalline mass (33 mm max.) at indicated crystallization temperature (°C.) | | | | | | | | | | | | | | | |
|---|---|---|---|---|---|---|---|---|---|---|---|---|---|---|---|---|---|
| | | A-1[a] | | | | A-2 | | | | A-3 | | | | A-4 | | | |
| | | 16 | 6 | −10 | −19 | 16 | 6 | −10 | −19 | 16 | 6 | −10 | −19 | 16 | 6 | −10 | −19 |
| 0.0[b] | 0 | 30 | 30 | 33 | 33 | | | | | | | | | | | | |
| | 1 | 10 | 26 | 28 | 30 | | | | | | | | | | | | |
| | 2 | 10 | 22 | 20 | 28 | | | | | | | | | | | | |
| | 3 | 10 | 22 | 15 | 24 | | | | | | | | | | | | |
| | 4 | 10 | 22 | 13 | 23 | | | | | | | | | | | | |
| 12.5 | 0 | [c] | 14 | 33 | 33 | [c] | 30 | 33 | 33 | [c] | 30 | 33 | 33 | 3 | 33 | 33 | 33 |
| | 1 | [c] | 9 | 4 | 10 | [c] | 14 | 3 | 5 | [c] | 10 | 2 | 4 | 2 | 20 | 6 | 18 |
| | 2 | [c] | 9 | 3 | 6 | [c] | 10 | 2 | 4 | [c] | 10 | 2 | 2 | 2 | 15 | 4 | 10 |
| | 3 | [c] | 9 | 3 | 5 | [c] | 10 | 1 | 3 | 0 | 10 | 1 | 2 | 1 | 15 | 4 | 7 |
| | 4 | [c] | 7 | 2 | 5 | 0 | 8 | [c] | 3 | | 6 | [c] | 2 | 1 | 12 | 3 | 7 |
| 25.0 | 0 | 0 | 4 | 33 | 33 | 0 | 2 | 33 | 33 | 0 | 2 | 33 | 33 | [c] | 7 | 33 | 33 |
| | 1 | | 4 | 0 | 1 | | 1 | 0 | 0 | | 1 | 0 | 0 | 0 | 7 | [c] | 3 |
| | 2 | | 4 | | [c] | | 1 | | | | [c] | | | | 7 | [c] | 1 |
| | 3 | | 4 | | 0 | | [c] | | | | [c] | | | | 7 | 0 | [c] |
| | 4 | | 3 | | | | [c] | | | | 0 | | | | 7 | | [c] |
| 50.0 | 0 | 0 | 0 | 6 | 33 | 0 | 0 | 0 | 2 | 0 | 0 | [c] | 30 | 0 | [c] | 33 | 33 |
| | 1 | | | 0 | 0 | | | | 0 | | | 0 | 0 | | 0 | 0 | 0 |

[a]Esters of 4(and 5)-chloro-trans-2-methylcyclohexane-1-carboxylic acid: A-1, 1,1-dimethylpropyl ester; A-2, 1-methylbutyl ester; A-3, 1-methylpropyl ester; A-4, 1,1-dimethyl-2-propenyl ester.
[b]Trimedlure standard.
[c]A trace of crystals present.

EXAMPLE 2

The additives and trimedlure and the concentrations used were the same as described in Example 1. The initial dose for each lure was 0.2 ml.

Bioassay. Tests were conducted in a macadamia nut orchard at Keaau, Hawaii, according to the general method described in Leonhardt et al., *Journal of Economic Entomology* 77: 744–749 (1984).

The results are given in Table 2. As discussed in detail above, the data clearly demonstrate the ability of the additives (A) of the invention to significantly extend the attractiveness of trimedlure (TML).

TABLE 2

| | | Days aged | | | | | | | | |
|---|---|---|---|---|---|---|---|---|---|---|
| | | 11 | | | 14 | | | 18 | | |
| | | Mg/wick | | Mean[d] | Mg/wick | | Mean | Mg/wick | | Mean |
| | % A | TML | A | catch | TML | A | catch | TML | A | catch |
| A-1[b] | 0.0[c] | 35[d] | — | 49.53[a] | [e] | — | 4.49b | [e] | — | 0.00c |
| | 12.5 | 38[d] | 9[d] | 32.44[a] | 17 | 6 | 38.81[a] | <1 | <1 | 2.86[bc] |
| | 25.0 | 38[d] | 24[d] | 28.06[a] | 11 | 11 | 55.35[a] | 1 | 3 | 10.18[b] |
| | 50.0 | 27[d] | 49[d] | 43.94[a] | 11 | 27 | 60.84[a] | <1 | 6 | 43.69[a] |
| | 100.0 | — | 128[d] | 41.91[a] | — | 105 | 64.64[a] | — | 80 | 46.51[a] |
| A-2 | 0.0 | 22[d] | — | 43.51[a] | [e] | — | 0.08[c] | [e] | — | 0.06[c] |
| | 12.5 | 24[d] | 11[d] | 54.86[a] | 13 | 8 | 53.88[ab] | <1 | 2 | 12.46[b] |
| | 25.0 | 42[d] | 30[d] | 49.10[a] | 20 | 21 | 59.14[ab] | 5[d] | 12[d] | 27.98[a] |
| | 50.0 | 39[d] | 73[d] | 40.99[a] | 17 | 49 | 69.06[a] | 12 | 40 | 38.07[a] |

TABLE 2-continued

|  | % A | Mg/wick TML | A | Mean catch | Mg/wick TML | A | Mean catch | Mg/wick TML | A | Mean catch |
|---|---|---|---|---|---|---|---|---|---|---|
|  | 100.0 | — | 153[d] | 34.32[a] | — | 134 | 34.22[b] | — | 118 | 35.76[a] |
| A-3 | 0.0 | 38[d] | — | 24.78[a] | <1 | — | 0.29[c] | e | — | 0.00[c] |
|  | 12.5 | 28[d] | 7[d] | 43.96[a] | <1 | <1 | 18.66[b] | <1 | <1 | .00[c] |
|  | 25.0 | 37[d] | 19[d] | 31.43[a] | 8 | 7 | 25.50[ab] | e | e | .92[bc] |
|  | 50.0 | 24[d] | 41[d] | 33.99[a] | 8 | 18 | 47.33[a] | 3 | 12 | 5.48[b] |
|  | 100.0 | — | 103[d] | 23.23[a] | — | 76 | 30.25[ab] | — | 34 | 18.23[a] |
| A-4 | 0.0 | 12[d] | — | 53.82[a] | e | — | 0.58[b] | e | — | 0.00[b] |
|  | 12.5 | 29[d] | 8[d] | 39.13[ab] | 3 | 2 | 28.73[a] | e | e | 3.28[b] |
|  | 25.0 | 42[d] | 24[d] | 27.21[ab] | 13 | 12 | 43.82[a] | <1 | <1 | 13.03[a] |
|  | 50.0 | 39[d] | 67[d] | 23.59[b] | 15 | 38 | 41.60[a] | 5 | 20 | 23.62[a] |
|  | 100.0 | — | 115[d] | 30.18[ab] | — | 90 | 40.70[a] | — | 82 | 24.50[a] |

|  |  | Days aged |  |  |  |  |
|---|---|---|---|---|---|---|
|  |  | 21 |  |  | 23 |  |
|  |  | Mg/wick |  | Mean | Mg/wick |  | Mean |
|  | % A | TML | A | catch | TML | A | catch |
| A-1[b] | 0.0[c] | e | — | 84.27[af] | e | — | 95.65[af] |
|  | 12.5 | e | e | 0.00[c] | e | e | 0.00[c] |
|  | 25.0 | <1 | <1 | 31.25[b] | e | <1 | 7.24[c] |
|  | 50.0 | 1 | 10 | 87.98[a] | <1 | 6 | 51.12[b] |
|  | 100.0 | — | 62[d] | 103.43[a] | — | 51 | 76.04[ab] |
| A-2 | 0.0 | e | — | 141.61[af] | e | — | 98.21[af] |
|  | 12.5 | e | e | 23.52[c] | e | e | 0.50[c] |
|  | 25.0 | 2 | 8 | 53.14[bc] | <1 | 2 | 24.80[b] |
|  | 50.0 | 6 | 36 | 117.94[a] | 3 | 24 | 41.09[b] |
|  | 100.0 | — | 112 | 84.46[ab] | — | 92 | 54.61[ab] |
| A-3 | 0.0 | e | — | 95.65[af] | e | — | 108.58[af] |
|  | 12.5 | e | e | 0.00[c] | e | e | 0.00[c] |
|  | 25.0 | e | e | .00[c] | e | e | 0.00[c] |
|  | 50.0 | e | e | .00[c] | e | e | 1.25[c] |
|  | 100.0 | — | 26 | 60.37[b] | — | 7 | 39.82[b] |
| A-4 | 0.0 | e | — | 141.13[af] | e | — | 117.94[af] |
|  | 12.5 | e | e | 0.00[c] | e | e | 0.00[c] |
|  | 25.0 | e | e | 17.81[b] | e | e | 0.77[c] |
|  | 50.0 | 2 | 9 | 108.37[a] | <1 | 3 | 43.43[b] |
|  | 100.0 | — | 45 | 90.63[a] | — | 34 | 37.33[b] |

[a]The means are weighted means back calculated from a square root transformation of data. Catches followed by the same letter within a column and within an additive series are not significantly different (P < 0.05; Duncan's [1951] multiple range test).
[b]See footnote [a]Table 1 for additive (A) identification.
[c]Trimedlure (TML) standard.
[d]Wick not analyzed. Weight estimated graphically.
[e]Content <0.004 mg (limit of detection).
[f]Catch using a freshly baited wick.

EXAMPLE 3

1-Methylbutyl 4(and 5)-chloro-trans-2-methylcyclohexanecarboxylate (A-2) was synthesized as described in Example 1. The additive was mixed in a concentration of 25% with trimedlure (TML) (vol/vol).

Bioassay. The standard trimedlure and the mixture with a 25% concentration of A-2 were applied undiluted (2 ml) to cotton wicks (13 mm diam. ×50 mm length) and medflies were released at 0, 1, 2, 4, and 5 weeks. The rest of the test was the same as described in Example 2.

The results are given in Table 3. As shown in the first section, after two weeks, both lures are statistically equivalent; however at week 4 and 5, the trimedlure plus additive is statistically superior to trimedlure. As described above, the second section discloses even more clearly the extending properties of the additive.

TABLE 3

| Lure | 0 | 1 | 2 | 4 | 5 |
|---|---|---|---|---|---|
|  | Mean catch[a,b] at week |  |  |  |  |
| Trimedlure (TML) | 7.98a | 9.75a | 11.42a | 2.07b | 3.51b |
| TML + A-2 | 8.33a | 8.68a | 11.54a | 4.53a | 6.26a |
|  | Mg/wick at week |  |  |  |  |
| TML | 1823 | 1029 | 300 | <0.5 | <0.5 |
| TML in TML + A-2 | 1196 | 755 | 433 | 5 | <0.5 |

TABLE 3-continued

| Lure | 0 | 1 | 2 | 4 | 5 |
|---|---|---|---|---|---|
| A-2 in TML + A-2 | 322 | 261 | 214 | 43 | 3 |

[a]Catches followed by the same letter within a column are not significantly different (P < 0.05; Duncan's [1951] multiple range test).
[b]Mean of data transformed by $\sqrt{x + 0.5}$.

EXAMPLE 4

Additives. The following esters of 4(and 5)-chloro-trans-2-methylcyclohexane-1-carboxylic acid: 1-methylpropyl; 1-methylbutyl; 1,1-dimethyl-2-propenyl; 1,1-dimethylpropyl; 1-methyl-2-propenyl, and 1-cyclopropylethyl, were synthesized as described in Example 1.

The trimedlure used was as described in Example 1.

Bioassay. The chemicals were applied undiluted (50 μl) to cotton wicks (9.5 mm diam. ×12.7 mm length) and medflies were released at 0 and 7 days. The rest of the test was the same as described in Example 2 except for the use of 5 replicates in Test II.

The results of the attraction of additives of the invention to the medfly are given in Table 4. As can be seen, although five of the compounds are significantly less attractive than trimedlure at the beginning of the test, by day 8 all have become significantly more attractive than trimedlure.

TABLE 4

| Ester | Test I (10 replicates) | | | | 
|---|---|---|---|---|
| | Total catch Days aged | | Mean catch[a,b] Days aged | |
| | 1 | 8 | 1 | 8 |
| Trimedlure-Std. | 1748 | 190 | 12.96a | 4.26b |
| 1-Methylpropyl | 939 | 472 | 9.51b | 6.69a |
| 1-Methylbutyl | 751 | 458 | 8.34b | 6.47a |

| | Test II (5 replicates) | | | |
|---|---|---|---|---|
| | Total catch Days aged | | Mean catch Days aged | |
| | 1 | 8 | 1 | 8 |
| Trimedlure-Std. | 895 | 2 | 12.63a | 0.91d |
| 1,1-Dimethyl-2-propenyl | 784 | 488 | 12.10ab | 9.38a |
| 1,1-Dimethylpropyl | 473 | 694 | 9.38abc | 10.92a |
| 1-Methylbutyl | 389 | 578 | 8.10bc | 10.47a |
| 1-Methyl-2-propenyl | 295 | 102 | 7.48c | 4.51b |
| 1-Cyclopropylethyl | 188 | 94 | 5.88c | 4.20c |

[a] Catches followed by the same letter within a column are not significantly different ($P < 0.05$; Duncan's [1951] multiple range test).

[b] Mean of data transformed by $\sqrt{x + 0.5}$.

It is understood that the foregoing detailed description is given merely by way of illustration and that modification and variations may be made therein without departing from the spirit and scope of the invention.

Having thus described our invention, we claim:

1. In a method of attracting the mediterranean fruit fly which employs trimedlure as the attractant, wherein the improvement comprises employing the trimedlure with a crystallization inhibiting and attraction extending amount of a pure or substantially pure isomeric mixture of

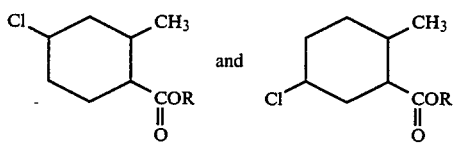

wherein —$CH_3$ and —COOR are in a trans-configuration and the Cl is in both an equatorial and axial conformation, and R is a $C_4$ to $C_6$ straight-or branched-chain alkyl or alkenyl group but not 1,1-dimethylethyl, a $C_1$ or $C_2$ straight-chain alkyl having a $C_3$ to $C_5$ alicyclic ring moiety, a $C_1$ or $C_2$ straight-chain alkyl having a $C_3$ to $C_5$ alicyclic ring moiety having a lower alkyl substituent, a $C_3$ to $C_6$ alicyclic ring, or a $C_3$ to $C_6$ alicyclic ring having a lower alkyl substituent.

2. The method of claim 1 wherein R is 1-methylpropyl.

3. The method of claim 1 wherein R is 1-methylbutyl.

4. The method of claim 1 wherein R is 1,1-dimethylpropyl.

5. The method of claim 1 wherein R is 1,1-dimethyl-2-propenyl.

6. The method of claim 1 wherein R is 1-methyl-2-propenyl.

7. The method of claim 1 wherein R is 1-methyl-3-butenyl.

8. The method of claim 1 wherein R is 1-ethyl-2-propenyl.

9. A composition which comprises trimedlure and a crystallization inhibiting and attraction extending amount of a pure or substantially pure isomeric mixture

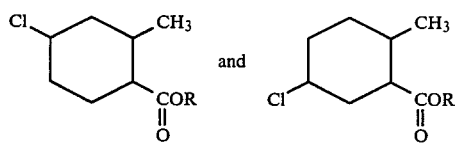

wherein —$CH_3$ and —COOR are in a trans-configuration and the Cl is in both an equatorial and axial conformation, and R is a $C_4$ to $C_6$ straight- or branched-chain alkyl or alkenyl group but not 1,1-dimethylethyl, a $C_1$ or $C_2$ straight-chain alkyl having a $C_3$ to $C_5$ alicyclic ring moiety, a $C_1$ or $C_2$ straight-chain alkyl having a $C_3$ to $C_5$ alicyclic ring moiety having a lower alkyl substituent, a $C_3$ to $C_6$ alicyclic ring, or a $C_3$ to $C_6$ alicyclic ring having a lower alkyl substituent and wherein said amount of said isomeric mixture is 12.5 to 50% v/v, additive/trimedlure.

10. The composition of claim 9 wherein R is 1-methylpropyl.

11. The composition of claim 9 wherein R is 1-methylbutyl.

12. The composition of claim 9 wherein R is 1,1-dimethylpropyl.

13. The composition of claim 9 wherein R is 1,1-dimethyl-2-propenyl.

14. The composition of claim 9 wherein R is 1-methyl-2-propenyl.

15. The composition of claim 9 wherein R is 1-methyl-3-butenyl.

16. The composition of claim 9 wherein R is 1-ethyl-2-propenyl.

17. The method of claim 1 wherein said amount of said added isomeric mixture is 12.5 to 50%, v/v, additive/trimedlure.

* * * * *